United States Patent [19]

Saccomano et al.

[11] Patent Number: 5,185,369
[45] Date of Patent: Feb. 9, 1993

[54] SYNTHETIC HETEROARYL POLYAMINES AS EXCITATORY AMINO ACID NEUROTRANSMITTER ANTAGONISTS

[75] Inventors: Nicholas A. Saccomano, Ledyard; Robert A. Volkmann, Mystic, both of Conn.

[73] Assignee: Pfizer Inc., New York, N.Y.

[21] Appl. No.: 749,038

[22] Filed: Aug. 23, 1991

[51] Int. Cl.$^5$ .................... A61K 31/295; C07F 17/02
[52] U.S. Cl. .................................. 514/502; 556/144; 556/145
[58] Field of Search ................. 556/144, 145; 514/502

[56] References Cited

PUBLICATIONS

CA 99: 88561m. Labeling of Biologically Active Peptides with Metallocenes: Substance P. Hublau et al. 1983.

Primary Examiner—Mary C. Lee
Assistant Examiner—Joseph K. McKane
Attorney, Agent, or Firm—Peter C. Richardson; J. Trevor Lumb; D. Stuart McFarlin

[57] ABSTRACT

Compounds having the formula $R\text{-}(CH_2)_m\text{-}CO\text{-}R'$ wherein R is ferrocene, a 5 to 7 member azacyclic system or an 8 to 11 member azabicyclic system, having 1 or 2 nitrogen atoms, or any such system substituted with one or more of F, Cl, Br, OH, C1 to C4 alkyl, C1 to C4 alkoxy, $CF_3$, phenyl, amino, C1 to C4 alkylamino and di(C1 to C4 alkyl)amino; m is 0 or 1; and R' is $-[NH(CH_2)_n]_xNH_2$, with each n being independently 2 to 5 and x being 1 to 6;

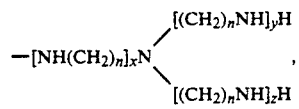

with each n being independently 2 to 5, x being 0 to 4, y and z being independently 1 to 5 and the sum of x and the greater of y and z being 1 to 5; or

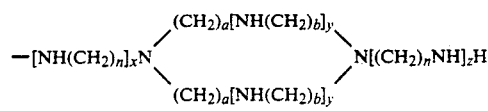

with each a being 2 to 5, each b being 2 to 5, each n being independently 2 to 5, x being 0 to 3, each y being 0 or 1, z being 0 to 3 and $x+y+z$ being 0 to 4, and their pharmaceutically acceptable acid addition salts are potent excitatory amino acid neurotransmitter antagonists. These compounds are useful as mammalian psychotherapeutants, as the active ingredient in pharmaceutical compositions for treating conditions in mammals which are mediated by excitatory amino acid neurotransmitters and in the control of invertebrate pests.

2 Claims, No Drawings

SYNTHETIC HETEROARYL POLYAMINES AS EXCITATORY AMINO ACID NEUROTRANSMITTER ANTAGONISTS

BACKGROUND OF THE INVENTION

This invention relates to a class of heteroaryl polyamines and the pharmaceutically acceptable salts thereof which are antagonists of excitatory amino acid neurotransmitters. These neurotransmitters affect neuronal cells of a variety of organisms including invertebrates and vertebrates. The polyamines of the present invention are synthetic analogs of certain polyamines found to be present in the venom of the *Agelenopsis aperta* spider. This invention also relates to the use of such polyamines and their salts in antagonizing excitatory amino acid neurotransmitters. These neurotransmitters affect cells such as cells in the nervous system of an organism. This invention further relates to the use of such polyamines and their salts in the treatment of excitatory amino acid neurotransmitter-mediated diseases and conditions in a mammal and in control of invertebrate pests, and to compositions comprising said polyamines and salts thereof. This invention also relates to methods of producing such polyamines.

It has been reported that the venom of the spider *Agelenopsis aperta* contains at least two toxins which affect calcium currents. Jackson, H., et al., Soc. Neu. Sci. Abstr. 12:1078 (1987). Those authors disclose a toxin, referred to therein as AG2, which has a molecular weight of less than 1,000 daltons and appears to suppress calcium currents in a broad range of tissues. Further, Jackson, H. et al., Soc. Neu. Sci. Abstr. 12:730 (1986) report another toxin from *Agelenopsis aperta* comprising a component of about 6,000 M.W. That toxin is reported to block presynaptic transmission and it has been suggested that the toxin blocks calcium channels associated with the release of neurotransmitter.

Certain polyamines found to be present in the venom of the *Agelenopsis aperta* spider are disclosed in U.S. Pat. No. 5,037,846, filed Apr. 28, 1989 and assigned to the assignees hereof. Those polyamines and the pharmaceutically acceptable salts thereof are disclosed therein as blockers of excitatory amino acid receptors in cells and one such polyamine, B₁ therein, is also disclosed as a blocker of calcium channels.

Compounds which are excitatory amino acid neurotransmitter antagonists have a variety of utilities. Excitatory amino acid neurotransmitter antagonists are useful in the treatment of such conditions as stroke, cerebral ischemia, neuronal degenerative disorders such as Alzheimer's disease and epilepsy and as psychotherapeutants, among others. See *Excitatory Amino Acids In Health and Disease*, D. Lodge, E., John Wiley and Sons Ltd., New York, NY. 1988, the teachings of which are incorporated herein by reference. Further, such compounds are useful in the study of the physiology of cells such as neuronal cells and in the control of invertebrate pests.

Glutamate is the major excitatory neurotransmitter in mammalian brain. There has been a great deal of excitement in the past decade as the developing pharmacology of glutamate receptors has suggested their differentiation into several subtypes. The glutamate receptor subtype classified by the selective action of the exogenous agonist N-methyl-Daspartate (NMDA) has been the subject of intense research since these receptors have been proposed to play a role in a variety of neurological pathologies including stroke, epilepsy, and neurodegenerative disorders such as Alzheimers's disease. There are currently two broad classes of NMDA receptor antagonists that are being aggressively pursued in search of clinically useful drugs. The first class consists of competitive antagonists which interfere with binding of glutamate to its receptor site. These compounds are characterized as highly polar compounds such as the phosphonate compounds AP7 and AP5. The highly charged structure of the competitive agents render them unable to penetrate the blood/brain barrier and limits their therapeutic utility. The second class consists of noncompetitive antagonists which block NMDA receptor function by acting at the ion channel associated with the NMDA receptor complex. These compounds include MK-801 and phencyclidine (PCP). The potential psychotomimetic effects of these classes of compounds are clear liabilities of the known drugs that work via these mechanisms.

Recently, a third class of antagonists have come under scrutiny, based on the identification of new glutamate antagonists from spider venoms. Arylamine structures isolated from the venom of *Agelenopsis aperta* that show potent and specific antagonism of mammalian NMDA receptors are disclosed in U.S. patent application Ser. No. 554,311, filed Jul. 17, 1990 and in U.S. Pat. No. 5,037,846, filed Jul. 31, 1990. The arylamines isolated from *Agelenopsis aperta* venom are composite structure built up from an aromatic acid and polyamine fragments bonded together by amide bonds. In these structures, some of the amines in the polyamine fragment are functionalized as N-hydroxy amines or quaternary ammonium salts. The chemical structures of the arylamines are distinct from the aforementioned standard competitive agents, AP5 or AP7, and the noncompetitive compound MK-801. For example, polyamine AGEL 416, disclosed in aforementioned U.S. Pat. No. 5,037,846, is disclosed as having the following structure.

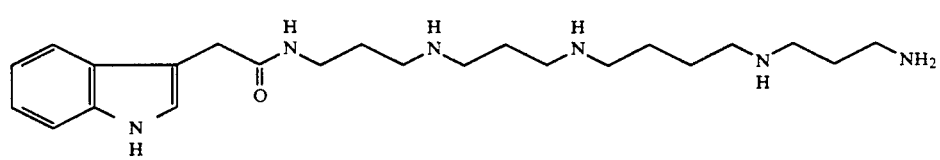

The mechanism of NMDA antagonism by these arylamines is also distinct from both the competitive and MK-801/PCP classes. Thus, spider venom arylamines provide a novel class of antagonist compounds at the NMDA receptor.

Given the benefit of the disclosure herein with respect to the naturally-occurring compounds it is now possible to obtain said compounds by methods other than through isolation/purification from whole venom of *Agelenopsis aperta*, and correspondingly, it is also possible to synthesize analogous compounds of the same class which are not naturally-occurring.

SUMMARY OF THE INVENTION

This application concerns a class of synthetic heteroaryl polyamines of the formula R—(CH$_2$)$_m$—CO—R', wherein R is a 5 to 7 member azacyclic system or an 8 to 11 member azabicyclic system having 1 or 2 nitrogen atoms, or any of the above substituted with one or more substituents independently selected from F, Cl, Br, OH, C1 to C4 alkyl, C1 to C4 alkoxy, CF$_3$, phenyl, amino, C1 to C4 alkylamino and di (C1 to C4) alkylamino; m is 0 or 1; R' is —[NH(CH$_2$)$_n$]$_x$NH$_2$; each n is independently 2 to 5; and x is 1 to 6, provided that when R is 3-indole and R' is —[NH(CH$_2$)$_3$]$_2$NH(CH$_2$)$_4$NH(CH$_2$)$_3$NH$_2$, then m is 0.

This invention also relates those compounds of the formula R—(CH$_2$)$_m$—CO—R', or a pharmaceutically acceptable acid addition salt thereof wherein R is a 5 to 7 member azacyclic system or an 8 to 11 member azabicyclic system having 1 or 2 nitrogen atoms, or any of the above substituted with one or more substituents independently selected from F, Cl, Br, OH, C1 to C4 alkyl, C1 to C4 alkoxy, CF$_3$, phenyl, amino, C1 to C4 alkylamino and di (C1 to C4) alkylamino; m is 0 or 1;

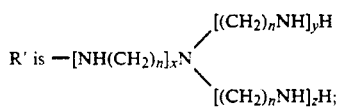

each n is independently 2 to 5; x is 0 to 4; y and z are each independently 1 to 5; and the sum of x and the greater of y and z is 1 to 5.

This application further relates to compounds of the formula R—(CH$_2$)$_m$—CO—R', or a pharmaceutically acceptable acid addition salt thereof wherein R is a 5 to 7 member azacyclic system or an 8 to 11 member azabicyclic system having 1 or 2 nitrogen atoms, or any of the above substituted with one or more substituents independently selected from F, Cl, Br, OH, C1 to C4 alkyl, C1 to C4 alkoxy, CF$_3$, phenyl, amino, C1 to C4 alkylamino and di (C1 to C4) alkylamino; m is 0 or 1; R is

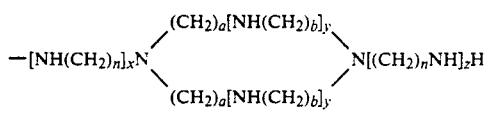

wherein each a is the same and is 2 to 5; each b is the same and is 2 to 5; each n is independently 2 to 5; x is 0 to 3; each y is the same and is 0 or 1; z is 0 to 3; and x+y+z is 0 to 4.

This invention still further relates to compounds of the formula

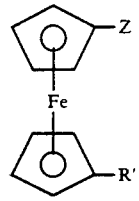

or the above substituted with one or more substituents independently selected from F, Cl, Br, OH, C1 to C4 alkoxy, CF$_3$, phenyl, amino, C1 to C4 alkylamino and di (C1 to C4) alkylamino, or a pharmaceutically acceptable acid addition salt thereof wherein Z is H or R'; R' is —(CH$_2$)$_m$CO[NH(CH$_2$)$_n$]$_x$NH$_2$; m is 0 or 1; each n is independently 2 to 5; and x is 1 to 6.

The azacyclic systems of the present invention can be saturated, unsaturated or aromatic, with the aromatic systems being preferred. With regard to the monocyclic systems, the six-membered rings are preferred, i.e., pyridine, pyridazine, pyrimidine and pyrazine. The bicyclic systems can be fused or bridged, with 9 to 10-membered fused systems being preferred, for example, indole, isoindole, the azaindoles, quinoline, isoquinoline, cinnoline, quinazoline, quinoxaline, pthalazine and the pyridopyridines. Of the aforementioned bicyclics, indole is particularly preferred.

Preferred R' groups are those wherein x is 4 or 5 and each n is independently 3 or 4. Particularly preferred R' groups are —[NH(CH$_2$)$_3$]$_5$—NH$_2$ and —[NH(CH$_2$)$_3$]$_3$—NH(CH$_2$)$_4$—NH(CH$_2$)$_3$—NH$_2$.

The polyamines of this invention and the pharmaceutically acceptable salts thereof are antagonists of excitatory amino acid neurotransmitters. Thus, said polyamines are useful in antagonizing such excitatory amino acid neurotransmitters, per se. The polyamines of this invention are also useful in the control of invertebrate pests and in the treatment of diseases and conditions in a mammal mediated by excitatory amino acid neurotransmitters. Said polyamines are useful also as mammalian psychotherapeutants.

This invention also concerns pharmaceutical compositions comprising said polyamines, methods of administering said polyamines and methods of making said polyamines.

DETAILED DESCRIPTION OF THE INVENTION

A synthetic scheme for production of a polyamine of the formula

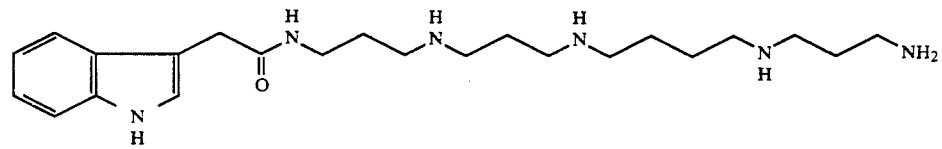

is shown in Reaction Schemes A to C, below.

REACTION SCHEME A

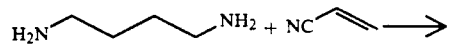

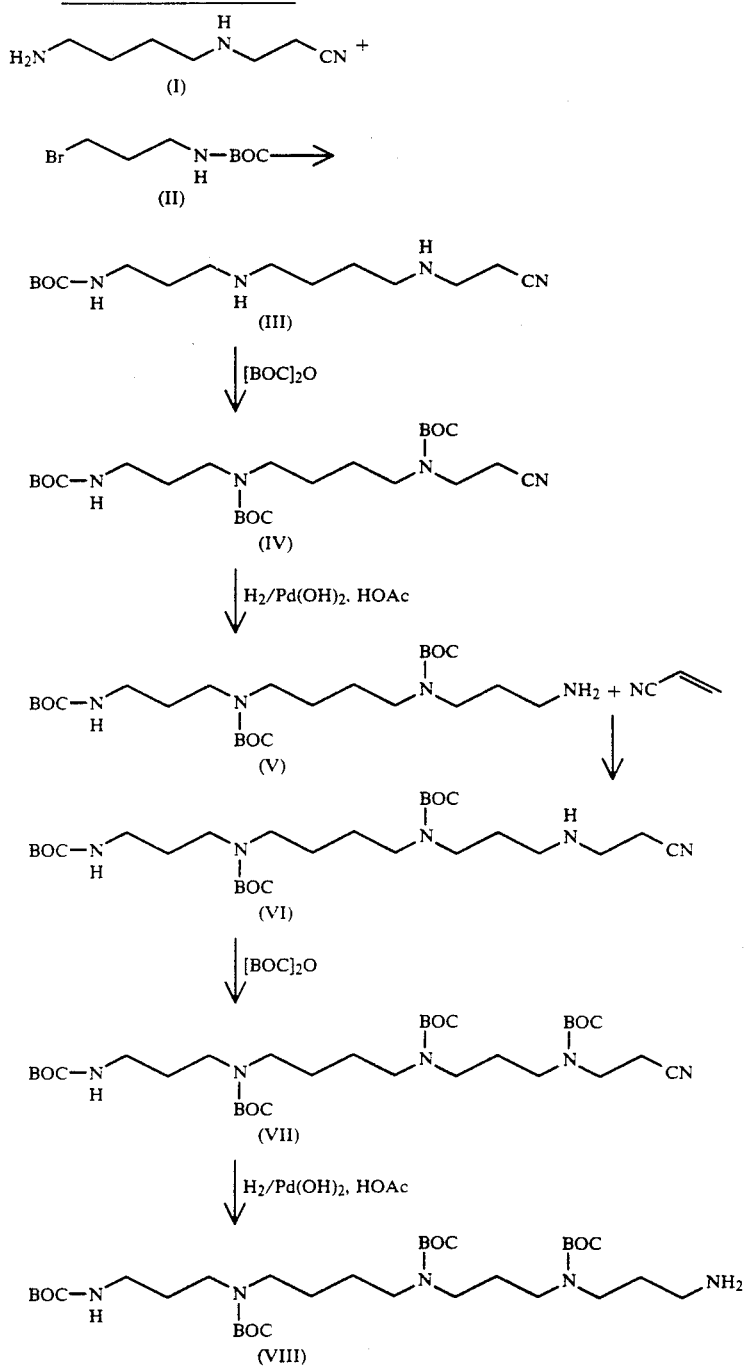
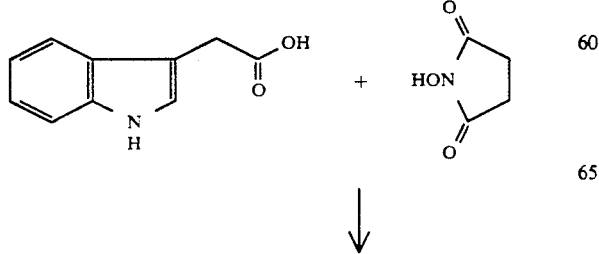
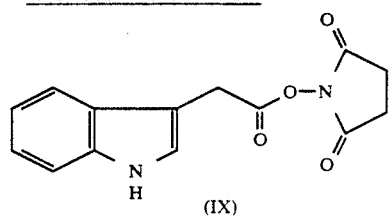

REACTION SCHEME C

IX + VIII ⟶

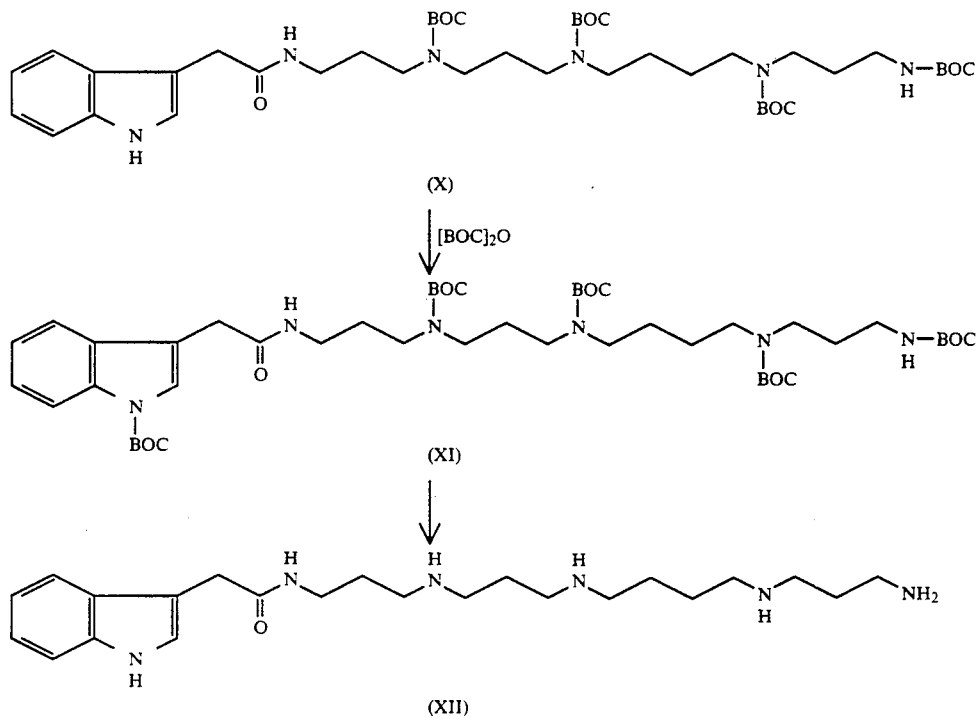

According to Reaction Scheme A, the polyamine intermediate compound of formula IV is prepared through a sequence of steps beginning with diaminobutane. Reaction conditions suitable to prepare the intermediate compound of formula VIII according to Reaction Scheme A are given in Example 5, parts 1 to 7. Reaction Scheme B illustrates a method for the preparation of the intermediate compound of formula IX. Reaction conditions suitable to prepare that intermediate are given in Example 5, part 8. Preparation of the polyamine compound of this invention of the formula XII is shown in Reaction Scheme C. Reaction conditions suitable for the coupling of the intermediate compounds of formulae VIII and IX and the subsequent preparation of the compound of formula XII are given in Example 5, parts 1 to 11.

The polyamines of this invention reversibly antagonize excitatory amino acid neurotransmitters, which neurotransmitters affect cells such as cells in the nervous system of a variety of organisms including invertebrates and vertebrates. The term vertebrates as used throughout is meant to include mammals. The term invertebrates as used throughout is meant to include for example, insects, ectoparasites and endoparasites.

The ability of the polyamines of the present invention to antagonize excitatory amino acid neurotransmitters is demonstrated by their ability to block N-methyl-D-aspartic acid (NMDA)-induced elevations of cGMP in neonatal rat cerebellums according to the following procedure. Cerebellums from ten 8-14 day old Wistar rats are quickly excised and placed in 4° C. Krebs/bicarbonate buffer, pH 7.4 and then chopped in 0.5 mm×0.5 mm sections using a McIlwain tissue chopper (The Nickle Laboratory Engineering Co., Gomshall, Surrey, England). The resulting pieces of cerebellum are transferred to 100 ml of Krebs/bicarbonate buffer at 37° C. which is continuously equilibrated with 95:5 $O_2/CO_2$. The pieces of cerebellum are incubated in such a manner for ninety minutes with three changes of the buffer. The buffer then is decanted, the tissue centrifuged (1 min., 3200 rpm) and the tissue resuspended in 20 ml of the Krebs/bicarbonate buffer. Then, 250 μl aliquots (approximately 2 mg) are removed and placed in 1.5 ml microfuge tubes. To those tubes are added 10 μl of the compound under study from a stock solution followed by 10 μl of 2.5 mM solution of NMDA to start the reaction. The final NMDA concentration is 100 μM. Controls do not have NMDA added. The tubes are incubated for one minute at 37° C. in a shaking water bath and then 750 μl of a 50 mM Tris-Cl, 5 mM EDTA solution is added to stop the reaction. The tubes are placed immediately in a boiling water bath for five minutes. The contents of each tube are then sonicated for 15 seconds using a probe sonicator set at power level three. Ten microliters are removed and the protein determined by the method of Lowry, Anal. Biochem. 100:201-220 (1979). The tubes are then centrifuged (5 min., 10,000×g), 100 μl of the supernatant is removed and the level of cyclic GMP (cGMP) is assayed using a New England Nuclear (Boston, Mass.) cGMP RIA assay according to the method of the supplier. The data is reported as pmole cGMP generated per mg. protein.

Further, the ability of the polyamines of the present invention to antagonize excitatory amino acid neurotransmitters is demonstrated by their ability to block NMDA/glycine induced increases in cytosolic free $[Ca^{2+}]_i$ in dissociated cerebellar granule cells according to the following procedure. Cerebellar granule cells are prepared from the cerebellum of 8 day old rats (Wilkin, G. P. et al., Brain Res: 115: 181-199, 1976). Squares (1 cm²) of Aclar (Proplastics Inc., 5033 Industrial Ave., Wall, N.J., 07719) are coated with poly-L-lysine and placed in 12-well dishes that contain 1 ml of Eagles Basal Medium. The cells are dissociated and aliquots containing $6.25 \times 10^6$ cells are added to each well containing the squares of Aclar. Cytosine-beta-D-arabino furanoside (final concentration 10 μM) is added 24 hours post plating. The cells are used for fura2 analysis at 6, 7 and 8 days of culture. The cells (attached to the Aclar squares) are transferred to 12-well dishes containing 1 ml of 2 μM fura2/AM (Molecular Probes Inc., Eugene, OR 97402) in HEPES buffer (containing 0.1% bovine serum albumin, 0.1% dextrose, pH 7.4, magnesium-free). The cells are incubated for 40 minutes at 37° C.; the fura2/AM containing buffer was removed and replaced with 1 ml of the same buffer without fura2-/AM. To a quartz cuvette is added 2.0 ml of prewarmed (37° C.) buffer. The cells on the Aclar are placed in the cuvette and the cuvette is inserted in a thermostated (37° C.) holder equipped with a magnetic stirrer and the fluorescence is measured with a fluorescence spectrophotometer (Biomedical Instrument Group, University of Pennsylvania). The fluorescence signal is allowed to stabilize for about 2 minutes.

An increase in cytosolic free calcium, represented by an increase in fluorescence, is produced by the addition of 50 μM NMDA and 1 μM glycine. Then 5-20 μl of a stock solution of the compound under study in phosphate-buffered saline (PBS, pH 7.4) at appropriate concentrations are added to the cuvette. Calibration of the fluorescent signals and fura2/AM leakage correction are performed using the established procedures of Grynkiewicz, G. Et al., J. Biol. Chem. 260:3440 (1985). At the completion of each test, the maximum fluorescence value (Fmax) is determined by addition of ionomycin (35 μM) and the minimum fluorescence value (Fmin) is determined by the subsequent addition of EGTA (12 mM) to chelate calcium. Employing the foregoing procedure, the ability of a subject compound to antagonize excitatory amino acid neurotransmitters is shown to occur by a decrease in fluorescence upon addition of the subject compound.

The polyamines of this invention are useful in antagonizing excitatory amino acid neurotransmitters, per se. As such, the polyamines are also useful in the control of invertebrate pests in the treatment of excitatory amino acid neurotransmitters-mediated diseases and conditions in a mammal such as stroke, cerebral ischemia, neuronal degenerative disorders such as Alzheimer's disease and epilepsy. Said polyamines also are useful as psychotherapeutants in a mammal. Further, the polyamines are useful in the study of the physiology of cells including, but not limited to, cells of the nervous system.

Also within the scope of this invention are the pharmaceutically acceptable salts of the polyamines of this invention. Such salts are formed by methods well know to those skilled in the art. For example, acid addition salts of the polyamines can be prepared according to conventional methods. Acid addition salts of the polyamines such as hydrochloric and trifluoroacetic acid addition salts thereof are preferred. Hydrochloric acid addition salts of the polyamines are particularly preferred.

When a polyamine of a pharmaceutically acceptable salt thereof of this invention is to be administered to a mammal, it can be administered alone or in combination with pharmaceutically acceptable carriers or diluents in a pharmaceutical composition according to standard pharmaceutical practice. The polyamines or pharmaceutically-acceptable salts thereof can be administered orally or parenterally. Parenteral administration includes intravenous, intramuscular, intraperitoneal, subcutaneous and topical administration.

For oral use of a polyamine or a pharmaceutically acceptable salt thereof of this invention, the compound can be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents are lactose and dried corn starch. When aqueous suspensions are required for oral use, the active ingredient is combined with emulsifying and suspending agents. If desired, certain sweetening and/or flavoring agents can be added.

For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled to render the preparation isotonic.

When a polyamine or salt thereof of this invention is used in a human subject, the daily dosage will normally be determined by the prescribing physician. However, suitable dosages for the polyamines of this invention are from about 1 to 30 mg/kg/day. Moreover, the dosage will vary according to the age, weight and response of the individual patient, as well as the severity of the patients's symptoms and the potency of the particular compound being administered. Therefore, dosages outside the range given above are possible and are within the scope of this invention.

When a polyamine or salt thereof of this invention is used in control of invertebrate pests, said compound is administered to said invertebrate directly or provided to the environment of said invertebrate. For example, a compound of this invention can be sprayed as a solution onto said invertebrate. The amount of compound necessary for control of said invertebrate will vary according to the invertebrate and environmental conditions and will be determined by the person applying the compound.

When a polyamine or salt thereof of this invention is used in the physiological study of cells, said compound is administered to the cells according to methods well known to those skilled in the art. For example, said compound can be administered to cells in an appropriate physiological buffer. An appropriate concentration of the compounds of this invention for use in such studies is 100 μM. However, the concentration of said compounds in such studies may be greater than or much less than 100 μM. The amount of the compound administered will be determined by the person skilled in the art according to the well known methods.

EXAMPLES

Procedure Types found in Experimentals (A) Protection of secondary amine with di-tert-butyl dicarbonate
(B) Cyanoethylation of primary amine
(C) Catalytic hydrogenation of nitrile to primary amine
(D) Amide bond-forming reactions (D1) Dimethylaminopropyl, ethyl carbodiimide/hydroxybenztriazole (D2) Dicyclohexylcarbodiimide/hydroxybenztriazole (D3) Dimethylaminopropyl, ethyl carbodiimide/hydroxy benztriazole/triethylamine (E) Deprotection of N-Boc substrates with HCl in dioxane (F) Deprotection of N-Boc substrates with TFA (trifluoroacetic acid)

(G) Alkylation of amines with N-Boc-3-bromopropylamine

EXAMPLE 1

Preparation of $H_2N[(CH_2)_3NH]_x$ Polyamine Side Chain

Step 1—Procedure Type B

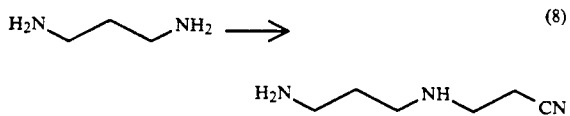

A 103 g sample of 1,3-diaminopropane was combined with 45 ml of MeOH with stirring at 4° C. Acrylonitrile (100 ml, 81 g, 1.1 eq) was dripped into the solution via pressure-equilibrating addition funnel over 90 minutes. After 3 hrs, a 500 mg portion was removed and evaluated by $^{13}C$ NMR; no 1,3-diaminopropane was observed. The crude material, containing the product aminonitrile 8, was distilled under reduced pressure and three fractions were collected in the 100°–125° C. temperature range of the distillation; all were clean enough to proceed to the reaction with di-tert-butyl carbonate and subsequent silica gel chromatographic purification.

$^1H$ NMR (250 MHz, CDCl$_3$) δ 2.67 (t, 2H, J=6.6 Hz), 2.54–2.43 (m, 4H), 2.28 (t, 2H, J=6.6 Hz), 1.37 (m, 2H, J=6.7 Hz), 1.05 (s, 3H); $^{13}C$ NMR (63.1 MHz, CDCl$_3$) δ 118.8, 46.9, 44.9, 40.2, 33.4, 18.5.

Step 2—Procedure Type A

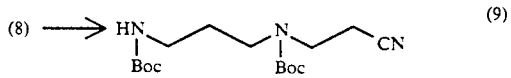

To a solution of aminonitrile 8 (23 g, 0.18 mol) in 500 ml of methylene chloride at 0° C. was added di-tert-butyl dicarbonate (80 g, 0.36 mol, 2 eq). The reaction mixture was stirred at room temperature for 16 hours and treated with an additional portion of di-tert-butyl dicarbonate (8 g, 0.036 mol). After stirring an additional 4 hours, the reaction was washed with 1N KOH (2×60 ml), dried over K$_2$CO$_3$, filtered and concentrated in vacuo. The product was purified by flash chromatography (SiO$_2$, 20→100% ethylacetate in hexane) to provide the product N-Boc-nitrile 9 as a clear oil (14 g, 24% yield).

$^1H$ NMR (250 MHz, CDCl$_3$) δ 3.40 (t, 2H, J=6.7 Hz), 3.28 (t, 2H, J=6.6 Hz), 3.05 (bs, 2H), 2.63–2.46 (m, 2H), 1.70–1.56 (m, 2H), 1.42 (s, 9H), 1.38 (s, 9H); $^{13}C$ NMR (63.1 MHz, CDCl$_3$) δ 155.8, 155.1, 118.5, 80.7, 78.9, 45.7, 44.4, 43.4, 32.4, 28.3, 28.2.

Step 3—Procedure Type C

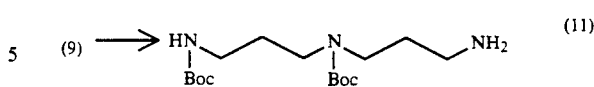

N-Boc nitrile 9, (49 g, 0.4 mol), 1000 ml acetic acid and 20 g (20 wt. % Pd(OH)$_2$) Pd(OH)$_2$/C were placed in a 2.6 l Parr shaker bottle. The bottle was filled with hydrogen gas to 50 psi and shaken for 4 hours. The reaction was filtered through a 0.47μ filter paper and concentrated in vacuo. The residue was dissolved in 1.5 l CH$_2$Cl$_2$ and washed with 1N KOH (2×200 ml). The base layers were extracted with CH$_2$Cl$_2$ (400 ml); the CH$_2$Cl$_2$ layers were combined, dried over K$_2$CO$_3$, filtered and concentrated in vacuo to yield the N-Boc amine 11 as a clear colorless oil (43 g, 86% yield).

$^1H$ NMR (250 MHz, CDCl$_3$) δ 3.28–3.12 (m, 2H), 3.11–3.00(m, 4H), 2.64 (t, 2H, J=7 Hz), 1.65–1.50 (m, 4H), 1.42 (s, 9H), 1.38 (s, 9H); $^{13}C$ NMR (63.1 MHz, CDCl$_3$) δ 155.8, 79.3, 78.5, 44.0, 43.4, 39.2, 32.3, 31.6, 28.5, 28.2.

Step 4—Procedure Type B

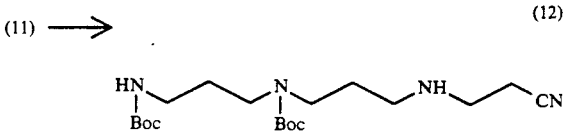

A 38 g sample of N-Boc amine 11 (0.114 mol) was combined with 6.7 g acrylonitrile (0.126 mol, 1.1 eq) in 60 ml methanol and stirred for 11 hours. Solvents were removed to yield 43 g (100% yield) of nitrile 12 as a clear colorless oil which was used without further purification.

$^1H$ NMR (250 MHz, CDCl$_3$) δ 3.18 (bs, 4H), 3.03 (m, 2H), 2.85 (t, 2H, J=6.6 Hz), 2.57 (t, 2H, J=6.7 Hz), 2.45 (t, 2H, J=6.7 Hz), 1.72–1.53 (m, 4H), 1.41 (s, 9H), 1.38 (s, 9H); $^{13}C$ NMR (63.1 MHz, CDCl$_3$) δ 155.9, 118.6, 79.6, 78.9, 46.3, 45.0, 43.9, 37.4, 28.8, 28.3, 18.6.

Step 5—Procedure Type A

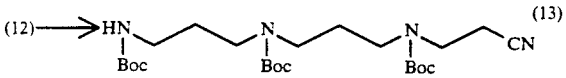

A 43 g sample of above-prepared nitrile 12 (0.114 mol) was combined with di-tert-butyl dicarbonate (25.6 g, 0.120 mmol, 1.05 eq) and 350 ml CH$_2$Cl$_2$ at 0° C. and stirred for 9 hours. Thin layer chromatography (TLC) (EtOAc, KMnO$_4$) showed no starting material remaining; reaction was purified in the same manner as N-Boc-nitrile 9. N-Boc-nitrile 13 was recovered as a clear, colorless oil (34 g, 63% yield).

$^1H$ NMR (250 MHz, CDCl$_3$) δ 3.45 (t, 2H, J=6.6 Hz), 3.39–2.97 (m, 8H), 2.68–2.46 (2, 2H), 1.82–1.56 (m, 4H), 1.44 (s, 18H), 1.87 (s, 9H); $^{13}C$ NMR (75.7 MHz, CDCl$_3$) δ 155.9, 80.5, 79.7, 78.9, 46.5, 44.5, 43.9, 37.6, 28.4, 28.3, 16.9.

Step 6—Procedure Type C

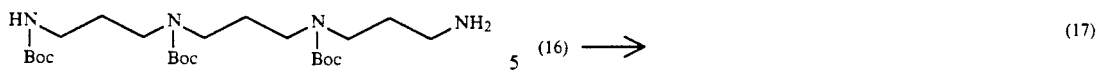

N-Boc-amine 14 was prepared from N-Boc-nitrile 13 as N-Boc-amine 11 was prepared from N-Boc-nitrile 9 in 99% yield (30 g).

$^1$H NMR (300 MHz, CDCl$_3$) δ 3.32–2.94 (m, 10H), 2.62 (t, 2H, J=6.7 Hz), 1.76–1.52 (m, 6H), 1.39 (s, 18H), 1.37 (s, 9H), 1.25 (s, 2H); $^{13}$C NMR (63.1 MHz, CDCl$_3$) δ 155.5, 79.5, 79.3, 45.5–43.7, 39.1, 37.3, 32.3, 28.3.

Step 7—Procedure Type B

(14) ⟶ (15)

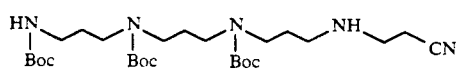

Nitrile 15 was prepared from N-Boc-amine 14 as nitrile 12 was prepared from N-Boc-amine 11 in 90% yield.

$^1$H NMR (300 MHz, CDCl$_3$) δ 3.29–3.02 (m, 14H), 2.86 (t, 2H, J=6.7 Hz), 2.57 (t, 2H, J=6.6 Hz), 2.46 (t, 2H, J=6.6 Hz), 1.72–1.57 (m, 6H), 1.41 (s, 9H), 1.40 (s, 9H), 1.39 (s, 9H); $^{13}$C NMR (75.7 MHz, CDCl$_3$) δ 155.5, 155.0, 118.7, 79.6, 79.5, 46.7–46.0, 45.2–43.3, 38.0–36.9, 28.4, 18.7. $^{13}$C NMR (300 MHz, CDCl$_3$) of nitrile 15 is indistinguishable from that of nitrile 12.

Step 8—Procedure Type A

(15) ⟶ (16)

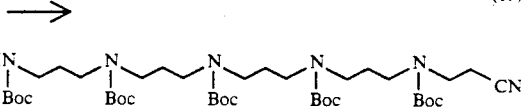

N-Boc-nitrile 16 was prepared from nitrile 15 as N-Boc-nitrile 13 was prepared from nitrile 12 as a clear colorless oil (30 g, 87% yield).

$^1$H NMR (300 MHz, CDCl$_3$) δ 3.36 (t, 2H, J=6 Hz), 3.18–2.90 (m, 14H), 2.57–2.42 (m, 2H), 1.72–1.48 (m, 6H), 1.40–1.28 (m, 27H).

Step 9—Procedure Type C

(16) ⟶ (17)

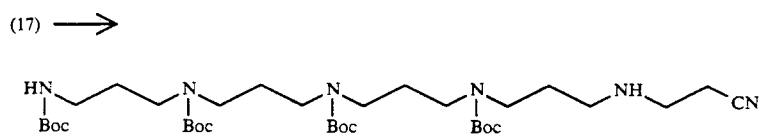

N-Boc-amine 17 was prepared from N-Boc-nitrile 16 as N-Boc-amine 11 was prepared from N-Boc-nitrile 9 in 74% yield (2.61 g).

$^1$H NMR (250 MHz, CDCl$_3$) δ 3.39–2.97 (m, 14H), 2.63 (t, 2H, J=6.6 Hz), 1.80–1.53 (m, 8H), 1.39 (s, 27H), 1.38 (s, 9H), 1.23 9 (s, 2H).

Step 10—Procedure Type B

(17) ⟶ (18)

Nitrile 18 was prepared from N-Boc-amine 17 as nitrile 12 was prepared from N-Boc-amine 11 in 91% yield (19 g), and was used without further purification.

$^1$H NMR (300 MHz, CDCl$_3$) δ 3.24–2.94 (m, 14H), 2.87 (t, 2H, J≈6 Hz), 2.57 (t, 2H, J≈6 Hz), 2.47 (t, 2H, J≈6 Hz), 1.74–1.54 (m, 8H), 1.45–1.36 (m, 36H).

Step 11—Procedure Type A

(18) ⟶ (19)

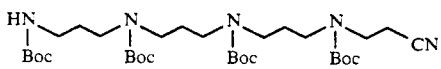

N-Boc-nitrile 19 was prepared from nitrile 18 as N-Boc-nitrile 13 was prepared from nitrile 12 (16 g, 74% yield).

$^1$H NMR (250 MHz, CDCl$_3$) δ 3.43 (t, 2H, J=6.6 Hz), 3.28–3.02 (m, 16H), 2.62–2.50 (m, 2H), 1.80–1.56 (m, 8H), 1.43 (s, 9H), 1.42 (s, 9H), 1.41 (s, 18H), 1.39 (s, 9H).

Step 12—Procedure Type C

(19) ⟶ (20)

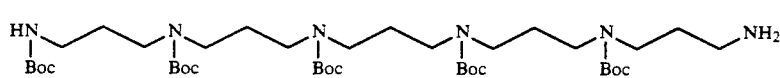

N-Boc-amine 20 was prepared from N-Boc-nitrile 19 as N-Boc-amine 11 was prepared from N-Boc-nitrile 9 (17 g, 99% yield).

$^1$H NMR (300 MHz, CDCl$_3$) δ 3.24–2.95 (m, 18H), 2.6 (t, 2H, J≈6H), 1.72–1.52 (m, 10H), 1.42–1.32 (m, 45H).

Step 13—Procedure Type B

(20) ⟶ (21)

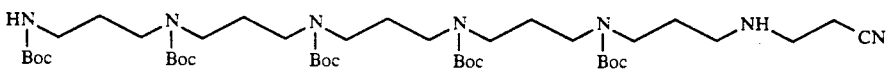

Nitrile 21 was prepared from N-Boc-amine 20 as nitrile 12 was prepared from N-Boc-amine 11 in 99% yield.

¹H NMR (250 MHz, CDCl₃) δ 3.32–3.03 (m, 16H), 2.91 (t, 2H, J=6.7 Hz), 2.61 (t, 2H, J≈6 Hz), 2.51 (t, 2H, J=6.6 Hz), 1.82–1.57 (m, 10H), 1.44 (s, 36H), 1.43 (s, 9H).

Step 14—Procedure Type A

(21) ⟶

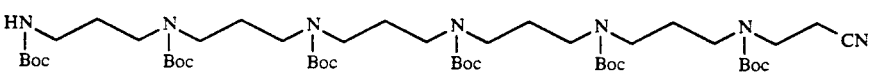

(22)

N-Boc-nitrile 22 was prepared from nitrile 21 as N-Boc-nitrile 13 was prepared from nitrile 12 in 99% yield.

3.45 ppm (t, 2H, J=6.6 Hz), 3.26–3.02 (m, 18H), 2.65–2.53 (m, 2H), 1.79–1.55 (m, 10H), 1.43 (s, 9H), 1.42 (s, 9H), 1.41 (s, 18H), 1.40 (s, 9H); ¹³C NMR {¹H} (250 MHz, CDCl₃) δ 155.2, 79.3, 44.7, 28.3, 28.3, 28.2.

Step 15—Procedure Type C

(22) ⟶

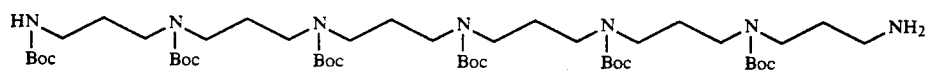

(23)

N-Boc-amine 23 was prepared from N-Boc-nitrile 22 as N-Boc-amine 11 was prepared from N-Boc-nitrile 9 (8 g, 99% yield).

¹H NMR (300 MHz, CDCl₃) δ 3.32–2.98 (m, 22H), 2.65 (t, 2H, J=6.6 Hz), 1.78–1.53 (m, 12H), 1.41 (s, 54H), 1.40 (s, 9H).

Step 16—Procedure Type B

(23) ⟶

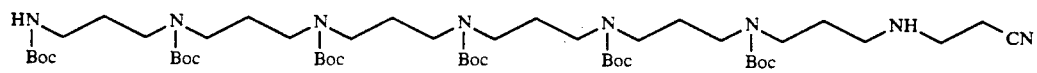

(24)

Nitrile 24 was prepared from N-Boc-amine 23 as nitrile 12 was prepared from N-Boc-amine 11 in 99% yield.

¹H NMR (250 MHz, CDCl₃) δ 3.32–0.304 (m, 22H), 2.90 (t, 2H, J=6.7 Hz), 2.61 (t, 2H, J≈6 Hz), 2.53 (t, 2H, J=6.7 Hz), 1.82–1.57 (m, 12H), 1.44 (s, 45H), 1.43 (s, 9H).

Step 17—Procedure Type A

(24) ⟶

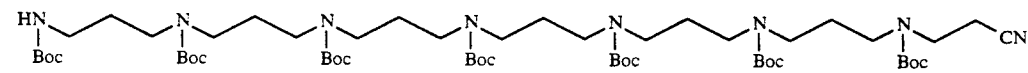

(25)

N-Boc-nitrile 25 was prepared from nitrile 24 as N-Boc-nitrile 13 was prepared from nitrile 12 (5.5 g, 74% yield).

¹H NMR (250 MHz, CDCl₃) δ 3.45 (t, 2H, J≈6.7 Hz), 3.40–2.97 (m, 24H), 2.66–2.51 (m, 2H), 1.80–1.55 (m, 12H), 1.54–1.30 (s, 63H).

Step 18—Procedure Type C

(25) ⟶

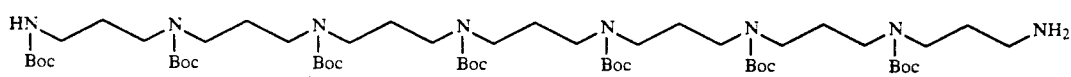

(26)

N-Boc-amine 26 was prepared from N-Boc-nitrile 25 as N-Boc-amine 11 was prepared from N-Boc-nitrile 9 (5.01 g, 91% yield).

¹H NMR (250 MHz, CDCl₃) δ 3.30–2.97 (m, 26H), 2.60 (t, 2H, J=6 Hz), 1.81 1.57 (m, 14H), 1.53–1.28 (m, 63H). ¹³C NMR (250 MHz, CDCl₃) δ 155.2, 79.3, 44.7, 28.7, 28.4, 27.5.

EXAMPLE 2

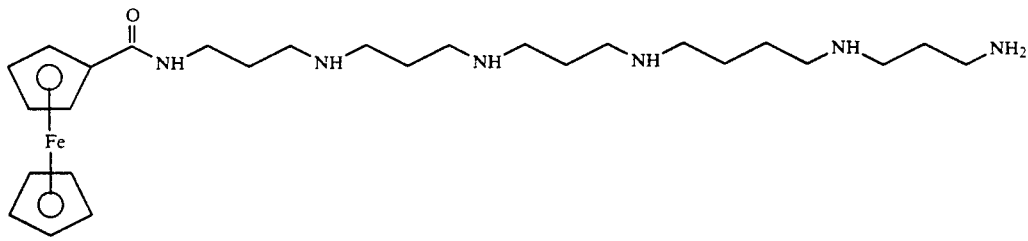

Step 1, Amide Bond Formation—Procedure Type D1

In a 50 ml one neck RBF were combined 0.19 g ferrocene carboxylic acid (0.82 mmol, 1.1 eq), 0.12 g hydroxybenzotriazole (0.89 mmol, 1.2 eq), 0.17 g 1-(3-Dimethylaminopropyl)-3-ethylcarbodiimide (HCl salt, 0.90 mmol, 1.2 eq) and 10 ml $CH_2Cl_2$ with stirring under dry $N_2$ atmosphere. After 30 minutes, 0.61 g of N-Boc-amine 27 (0.75 mmol, 1.0 eq., see Example 5a herein for preparation) was added to the solution. TLC (2×MeOH, $I_2$) indicated N-Boc-amine had been consumed after 2 hours. The reaction was diluted to 400 ml with EtOAc and washed with pH 4 buffer (2×25 ml), 25 ml $H_2O$, 1N KOH (2×25 ml), 25 $H_2O$ and 50 ml brine. The EtOAc layer was dried over $Na_2SO_4$, filtered and the solvents were removed to yield 712 mg (93%) of product as an orange oil.

$^1$H NMR (250 MHz, $CDCl_3$) δ 4.78 (s, 2H), 4.32 (t, 2H, J=1.8 Hz), 4.19 (s, 5H), 3.45-3.04 (m, 20H), 1.83-1.59 (m, 12H), 1.50 (s, 9H), 1.45 (s, 18H). 1.44 (s, 9H), 1.43 (s, 9H).

Step 2, Polyamine Deprotection—Procedure Type F

Trifluoroacetic acid (30 ml) was degassed with a dry $N_2$ bubble stream (via Teflon tubing) in a 100 ml one neck RBF at 0° C. The ferrocene carboxamide polyamine of step 1 above (712 mg, 0.69 mmol) was dissolved in 2 ml $CH_2Cl_2$ and transferred to the stirring TFA with 3×2 ml $CH_2Cl_2$ rinses. After 30 minutes, the ice bath was removed; after an additional 30 minutes, the solvents were removed under reduced pressure, then by Hi-Vac. The reddish brown oil remaining was mashed with $Et_2O$ (3×30 ml); a yellow solid formed and was collected under positive $N_2$ pressure on a porosity "B" frit. The solid was rinsed with ether and the residual ether was driven off by positive $N_2$ pressure to yield 690 mg (93% yield) of product as a solid.

$^1$H NMR (DMSO) δ 4.71 (t, 2H, J=1.73 Hz), 4.38 (t, 2H, J≈2 Hz), 4.15 (s, 5H), 3.28-3.21 (m, 2H), 3.03-2.81 (m, 18H), 2.04-1.72 (m, 8H), 1.61-1.50 (m, 4H); $^{13}$C NMR (250 MHz, $D_2O$) 177.3, 78.5, 76.1, 74.3, 49.7, 48.1, 47.3., 47.2, 47.1, 39.3, 38.8, 28.5, 26.5, 25.5, 25.4. HPLC (not less than) 96.08% pure; Novapak C18 column, 5-40% $CH_3CN/2\%/T.H_2O$ over 60 minutes, detected at 230 nm, elution time: 23.2 minutes. HRMS (FAB): (M+H) calculated for $C_{27}H_{48}N_6O$, 529.3328845; found 529.33172.

EXAMPLE 3

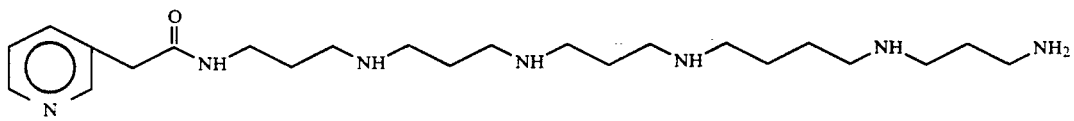

Step 1, Amide Bond Formation—Procedure Type D3

The hydrochloride salt of 2-pyridylacetic acid (0.105 g, 0.60 mmol, 1.0) was combined with 0.16 ml TEA (1.15 mmol, 2 eq) and 4 ml $CH_2Cl_2$. After 10 minutes, DEC (0.12 g, 0.62 mmol, 1.0 eq) and 0.09 g HOBt (0.66 mmol, 1.1 eq) were added and the mixture was stirred for 2 hours. N-Boc-amine 27 (0.44 g, 0.54 mmol, 0.9 eq) was added and reaction stirred an additional 10 hours. TLC (2×MeOH, $I_2$) indicated the N-Boc-amine had been consumed. The reaction was diluted to 400 ml with EtOAc, washed with 1N KOH (40 ml), brine (50 ml) and dried over $MgSO_4$. The EtOAc solution was filtered and the solvents removed to yield 0.4 g of a clear, green oil. The crude material was chromatographed from 10 g silica gel slurried in EtOAc with EtOAc as eluent. Appropriate fractions were combined and the solvents were removed to yield 0.20 g (40% yield) of a clear, light green oil.

$^1$H NMR (250 MHz, $CDCl_3$) δ 8.59-8.52 (m, $^1$H), 7.76-7.68) (m, 1H), 7.62-7.49 (m, $^1$H), 7.37 (d, $^1$H, J=8 Hz), 3.78 (s, 2H), 3.31-3.02 (m, 20H). 1.80-1.56 (m, 12H), 1.56-1.34 (m, 45H).

Step 2, Polyamine Deprotection—Procedure Type F

Trifluoroacetic acid (30 ml) was continuously degassed with a dry $N_2$ bubble stream (via Teflon tubing) in a 100 ml one neck RBF at room temperature. The 2-pyridylacetamide of step 1 above (180 mg) was dissolved in 2 ml $CH_2Cl_2$ and transferred to the stirring TFA. After 1 hour, the solvents were removed under reduced pressure and the residue was placed in Hi-Vac. The residue was mashed with ether (3×30 ml); a white solid formed and was collected under positive $N_2$ pressure on a porosity "B" frit. Remaining ether was removed by positive $N_2$ pressure; 169 mg (91% yield) of the product was isolated.

$^1$H NMR (250 MHz, $D_2O$) δ 8.48 (d, $^1$H, J=15 Hz), 7.98 (t, 1H, J=6 Hz), 7.51-7.47 (m, 2H), 3.86 (s, 2H), 3.32 (t, 2H, J≈9 Hz), 3.17-2.96 (m, 18H), 2.17-1.98 (m, 6H), 1.98-1.81 (m, 2H), 1.81-1.69 (m, 4H).

EXAMPLE 4

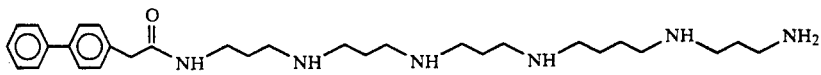

Step 1, Amide Bond Formation—Procedure Type D2

4-Biphenylacetic acid (53 mg, 0.25 mmol, 1.2 eq) was combined with 5 ml CH$_2$Cl$_2$, 84 μl triethylamine (0.6 mmol, 3 eq) 70 mg dicyclohexylcarbodiimide (0.34 mmol, 1.6 eq), 11 mg hydroxysuccinimide (0.09 mmol, 45 mol %) and 175 mg N-Boc-amine 27 (0.21 mmol, 1.0 eq). TLC (2×MeOH, KMnO$_4$) indicated the N-Boc-amine had been consumed after 16 hours. The reaction was diluted to 100 ml with CH$_2$Cl$_2$ and washed with aqueous 20% NH$_4$OH (2×100 ml). The base layers were extracted with CH$_2$Cl$_2$ (3×50 ml); all the CH$_2$Cl$_2$ fractions were combined, then washed with brine (50 ml) dried over K$_2$CO$_3$, filtered and the solvents removed to yield 281 mg (>100% yield) crude material. Pure product was isolated via flash silica gel chromatography (12 g slurried in CH$_2$Cl$_2$ and eluted with a 0–10% MeOH/CH$_2$Cl$_2$ gradient) as a white, waxy, solid (190 mg, 88% yield).

$^1$H NMR (250 MHz, CDCl$_3$) δ 7.56–7.50 (m, 4H), 7.43–7.28 (m, 5H), 3.56 (s, 2H), 3.26–2.98 (m, 20H), 1.78–1.52 (m, 12H), 1.48–1.36 (m, 45H).

Step 2, Polyamine Deprotection—Procedure Type F

Triflouroacetic acid (30 ml) was degasssed with a continuous N$_2$ bubble stream (via Teflon tubing) at 0° C. The biphenylacetamine of step 1 above (150 mg, 0.15 mmol) was added as a dry powder to the stirring TFA. After 40 minutes, the ice bath was removed; after an additional 20 minutes the solvents were removed under reduced pressure, then Hi-Vac. After 2 hours, the resulting tan oil was mashed with Et$_2$O (3×30 ml); a white solid formed and was collected under positive N$_2$ pressure on a porosity "C" frit. The solid was dissolved in water, rinsed through the frit and freeze dried to yield 136 mg (99% yield) of product as a white solid.

$^1$H NMR (300 MHz, D$_2$O) δ 7.62–7.56 (m, 5H), 7.4 (t, 2H, J=7.5 Hz), 7.38–7.31 (m, 2H), 3.45 (s, 2H), 3.13 (t, 2H, J=6.7 Hz), 3.02–2.80 (m, 18H), 2.00–1.54 (m, 12H).

EXAMPLE 5

1H-Indole-3-acetamide-N-(16-amino-4,8,13-triazahexadec-1-yl

Step 1

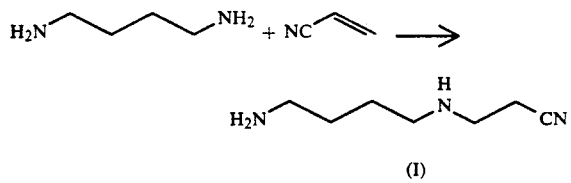

The compound of formula I was prepared from diaminobutane and acrylonitrile according to the published procedure of Yamamoto, Hisashi, J. Am. Chem. Soc. 103:6133–6136 (1981).

Step 2

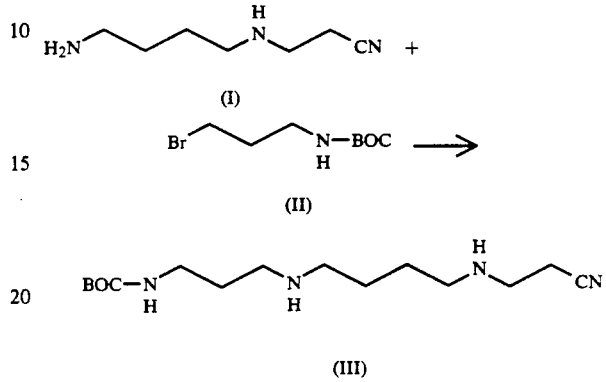

To a solution of N-cyanoethyl-1,4-diaminobutane (6.44 g, 0.0457 mol) in acetonitrile (200 ml) under a nitrogen atmosphere was added KF/Celite (11 g) followed by the dropwise addition over a 7 hour period of N-(tert-butoxycarbonyl)-3-bromopropylamine (10.87 g, 0.0457 mol). The reaction was allowed to stir for 16 hours at ambient temperature and was then heated to 70° C. for 24 hours. The reaction was allowed to cool and was filtered and concentrated in vacuo. The residue was dissolved in CH$_2$Cl$_2$ (200 ml), washed with 1N NaOH (100 ml), dried and concentrated in vacuo to afford crude product which was chromatographed on silica gel (using 9:1 CH$_2$Cl$_2$/MeOH) to afford 3.32 g of amine III.

$^1$H NMR (CDCl$_3$) δ 1.19–1.59 (m, 17H), 2.42 (t, J=6.6 Hz, 2H), 2.44–2.58 (m, 6H), 2.82 (t, J=6.6 Hz, 2H), 3.08 (m, 2H), 5.22 (br s, 1H); $^{13}$C NMR (CDCl$_3$) δ 18.68, 27.70, 27.74, 28.42, 29.94, 39.16, 45.03, 47.68, 48.99, 49.65, 78.78, 118.75, 156.11; HR FABMS observed (M+H) m/z=299.2434, C$_{15}$H$_{31}$N$_4$O$_2$ (req 299.2447).

Step 3

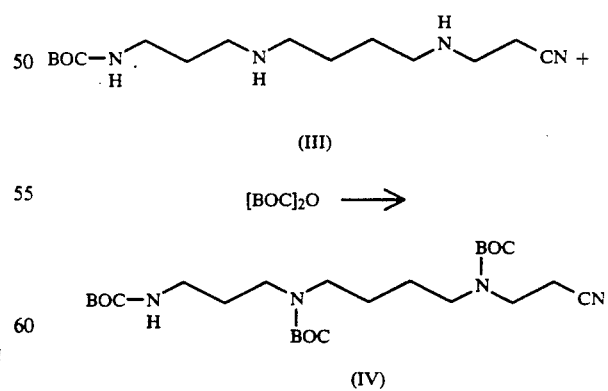

Under nitrogen atmosphere, 4.7 g (15.8 mmoles) of compound of formula III, prepared as described in step 2, above, was dissolved in 150 ml of dichloromethane. Then, 7.56 g (34.7 mmoles) of di-tert-butyldicarbonate were added and the reaction mixture was stirred overnight at room temperature. The mixture was then concentrated in vacuo and chromatographed on 400 g of silica gel using 50:50 ethylacetate/hexane solvent. The fractions were monitored by TLC (50:50 ethylacetate/hexane). The reactions containing the product of formula IV were combined and concentrated in vacuo to yield 7.9 g of product as an oil.

$^1$H NMR (CDCl$_3$) δ 1.20-1.59 (m, 33H), 2.55 (m, 2H), 3.01-3.37 (m, 8H), 3.39 (t, J=6.6 Hz, 2H), 5.25 (br s, 1H); $^{13}$C NMR δ 17.21, 25.73, 25.94, 28.22, 28.24, 28.27, 37.91, 43.78, 44.24, 46.60, 47.95, 78.96, 79.57, 80.44, 155.01, 155.75, 155.98; HR FABMS observed (M+H) m/z=499.3501, C$_{25}$H$_{47}$N$_4$O$_6$ (req 499.3496).

Step 4

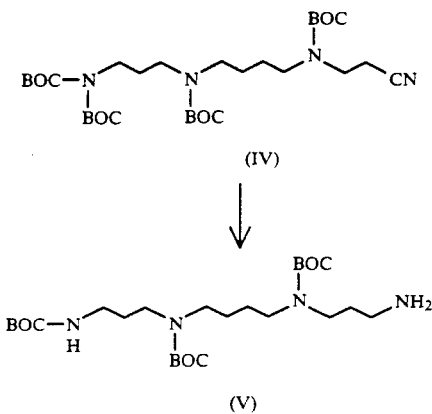

To 125 ml of acetic acid under a nitrogen atmosphere were added 7.85 g (15.8 mmoles) of compound of formula IV, prepared as described in step 3, above, and 6.5 g of Pd(OH)$_2$/carbon. The mixture was hydrogenated at 50 p.s.i. for 2 hours. The catalyst was removed by filtration and the filter cake was washed well with acetic acid. The filtrate was concentrated, taken up in 250 ml dichloromethane, washed twice with 100 ml of 1N NaOH and dried over K$_2$CO$_3$. The solution was filtered and the filtrate was concentrated in vacuo to yield 7.8 g of compound of formula V.

$^1$H NMR (CDCl$_3$) δ 1.24-1.59 (m, 35H), 2.14 (s, 2H), 2.61 (t, J=6.7 Hz, 2H), 2.98-3.14 (m, 10H), 5.22 (br s, 1H); $^{13}$C NMR (CDCl$_3$) δ 25.89, 28.42, 31.38, 32.36, 37.55, 38.95, 43.95, 46.65, 79.34, 79.48, 155.65, 156.03; HR FABMS observed (M+H) m/z=503.3804, C$_{25}$H$_{51}$N$_4$O$_6$ (req m/z=503.3809).

Step 5

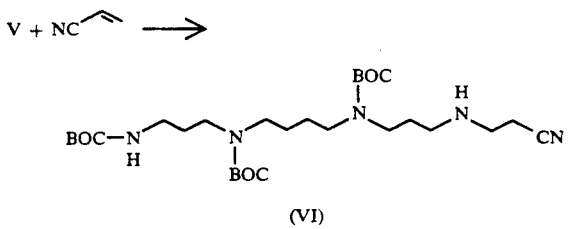

Under nitrogen atmosphere, 7.15 g (14.2 mmoles) of compound of formula V, prepared as described in step 4, above, was dissolved in 150 ml of methanol. Then, 1.03 ml (15.6 mmoles) of acrylonitrile was added and the reaction was stirred 72 hours at room temperature. The reaction mixture was then concentrated, reconcentrated three times from dichloromethane and stripped of solvent in vacuo to yield 7.65 g of product of formula VI as an oil.

$^1$H NMR (CDCl$_3$) δ 1.26.-1.73 (m, 36H), 2.44 (t, J=6.7 Hz, 2H), 2.54 (t, J=6.7 Hz, 2H), 2.83 (t, J=6.7 Hz, 2H), 3.00-3.16 (m, 10H), 5.24 (br s, 1H); $^{13}$C NMR (CDCl$_3$) δ 18.64, 25.84, 28.09, 28.43, 28.74, 37.84, 44.18, 44.68, 45.14, 46.29, 46.73, 46.85, 49.70, 78.90, 79.29, 79.46, 118.52, 155.84, 155.98; HR FABMS observed (M+H) m/z=556.4064, C$_{28}$H$_{54}$N$_5$O$_6$ (req m/z=556.4074).

Step 6

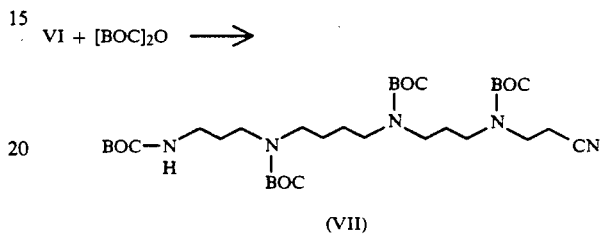

Under nitrogen atmosphere, 6.45 g (11.6 mmoles) of compound of formula VI, prepared as described in step 5, above, was dissolved in 125 ml of dichloromethane. To that solution were added 2.6 g (12 mmoles) of di-t-butyldicarbonate and the reaction mixture was stirred overnight at room temperature. The mixture was then concentrated in vacuo and chromatographed on 400 g of silica gel using 50:50 ethylacetate/hexane eluent. The product fractions were combined and concentrated to yield 6.6 g of product for formula VIII as an oil.

$^1$H NMR (CDCl$_3$) δ 1.26-1.73 (m, 44H), 3.03-3.24 (m, 14H), 3.42 (t, J=6.6 Hz, 2H), 5.25 (br s, 1H); $^{13}$C NMR (CDCl$_3$) δ 17.20, 25.88, 27.83, 28.12, 28.35, 28.45, 28.77, 37.87, 43.91, 44.20, 44.77, 46.27, 46.88, 78.94, 79.42, 79.50, 80.54, 117.91, 154.96, 155.44, 155.74, 155.99; HR FABMS observed (M+H) m/z=656.4579, C$_{33}$H$_{62}$N$_5$O$_8$ (req m/z=656.4598).

Step 7

VII →

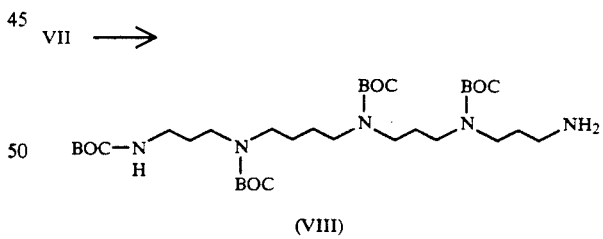

To 150 ml of acetic acid under a nitrogen atmosphere were added 6.6 g (10.1 mmoles) of compound of formula VII, prepared as described in step 6, above, and 6 g of Pd(OH)$_2$/carbon. The mixture was hydrogenated at 50 p.s.i. for 2 hours. The catalyst was removed by filtration and the filter cake was washed well with acetic acid. The filtrate was concentrated, taken up in 200 ml of dichloromethane, washed twice with 100 ml 1N NaOH and dried over K$_2$CO$_3$. The solution was filtered and the filtrate was concentrated in vacuo to yield 6.5 g of product of formula VIII.

$^1$H NMR (CDCl$_3$) 1.28-1.71 (m, 46H), 2.16 (br s, 2H), 2.65 (t, J=6.7 Hz, 2H), 3.01-3.18 (m, 14H), 5.24 (br s, 1H); $^{13}$C NMR (CDCl$_3$) δ 25.85, 27.66, 28.45, 28.76, 39.10, 44.21, 44.91, 46.80, 79.27, 79.46, 155.41, 155.67, 155.99; HR FABMS observed (M+H) m/z=660.4914, $C_{33}N_{66}N_5O_8$ (req 660.4911).

Step 8

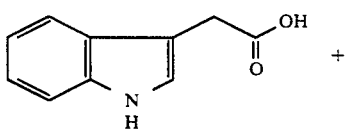

trate was concentrated to yield a foam. The foam was triturated with 75 ml of diethylether to yield a hard gum. Then, about 30 ml of ethylacetate was added followed by ethyl ether. The solids were isolated by filtration, washed with diethyl ether and dried under nitrogen to yield 1.74 g of product of formula IX. It was found that an additional 0.47 g of product could be obtained by treating the mother liquor with petroleum ether.

Step 9

IX + VIII ⟶

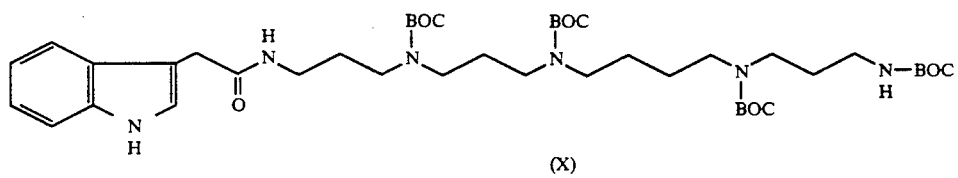

(X)

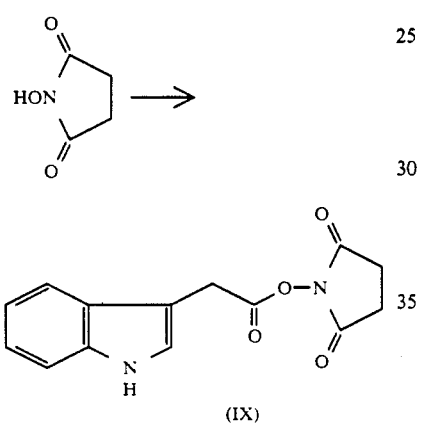

(IX)

Under nitrogen atmosphere, 0.33 g (5 mmoles) of compound of formula VIII, prepared as described in step 7, above, was dissolved in 10 ml of dichloromethane with stirring and then 0.136 g (5 mmoles) of compound of formula IX, prepared as described in step 8, above, were added. The reaction was stirred overnight at room temperature. The reaction mixture was then diluted out to 35 ml with dichloromethane, washed with 10 ml of 0.5N NaOH, dried over $K_2CO_3$, and concentrated. The concentrate was chromatographed on silica gel using 4:1 ethylacetate/hexane. The product fractions were concentrated to yield 0.37 g of a white foam containing product of formula X with some ethylacetate present.

Step 10

X + [BOC]$_2$O ⟶

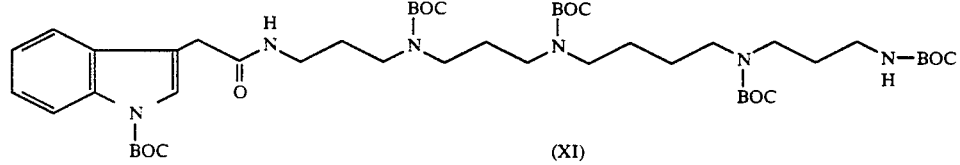

(XI)

Under a nitrogen atmosphere, 1.75 g (10 mmoles) of indole acetic acid, 1.15 g (10 mmoles) of N-hydroxysuccinimide and 2.06 g (10 mmoles) of dicyclohexylcarbodiimide were added to 75 ml of tetrahydrofuran. The reaction mixture was stirred at room temperature and a precipitate formed after about 5 minutes. After about 1.5 hours, the precipitate was removed by filtration, the filter cake was washed with 75 ml of tetrahydrofuran and the cake was air dried to yield 1.84 g. The combined filtrate was concentrated, taken up in ethylacetate and filtered, washing the filter with ethylacetate. The fil- Under nitrogen atmosphere, 0.37 g (0.45 mmoles) of compound of formula X, prepared as described in step 9, above, was dissolved in 10 ml of dichloromethane. Then 0.218 g (1 mmole) of di-t-butyldicarbonate were added followed by 12 ml (0.1 mmole) of 4-(N,N-dimethylamino)pyridine. The reaction was stirred at room temperature for 1 hour then allowed to stand overnight. The reaction mixture was chromatographed on silica gel using 4:1 ethylacetate/hexane and the product fractions were concentrated to yield 0.32 g of product of formula XI as a white foam.

Step 11

XI ⟶

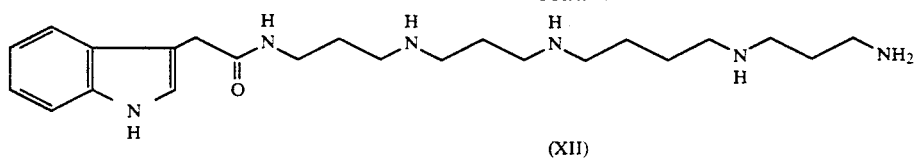

(XII)

Under nitrogen atmosphere, 0.32 g (0.35 mmoles) of compound of formula XI, prepared as described in part 10, above, were added to 15 ml of trifluoroacetic acid and stirred for 15 minutes. The reaction mixture was then concentrated in vacuo and triturated with diethylether to yield 0.30 g of product as a white powder.

By an analogous process, N-Boc amine 27, having the following structure, was made.

| Example | m | R |
|---------|---|----------|
| 6 | 0 | ferrocene |
| 7 | 1 | 3-indole |

EXAMPLES 8 TO 29

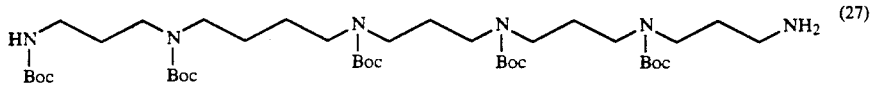

Steps 1 to 7, above, were followed, resulting in the N-Boc amine of formula VIII.

Step 8a

Starting with polyamine 27 and the appropriate R-acetic or carboxylic acid, compounds having the structure
$R(CH_2)_mCO[NH(CH_2)_3]_3NH(CH_2)_4NH(CH_2)_3NH_2 \cdot 5\text{-}$

(XIII)

Nitrile XIII was prepared from N-Boc amine VIII as nitrile VI was prepared from N-Boc amine V (Example 5, Step 5), giving 1.00 g of product (93% yield).

$^1$H NMR (CDCl$_3$) δ 1.26-1.66 (m, 47H), 2.45 (t, J=6.6 Hz, 2H), 2.56 (t, J=6.7 Hz, 2H), 2.85 (t, J=6.6 Hz, 2H), 3.01-3.30 (m, 14H), 5.25 (br s, 1H); $^{13}$C NMR (CDCl$_3$) δ 18.68, 25.92, 28.46, 28.48, 37.49, 44.19, 44.88, 45.16, 46.73, 78.93, 79.32, 79.44, 118.70, 155.46, 155.61, 156.04; HR FABMS observed (M+H) m/z=713.5191, C$_{36}$H$_{69}$N$_6$O$_8$ (req m/z=713.5177).

HCl (from procedure E) or $R(CH_2)_mCO[NH(CH_2)_3]_3NH(CH_2)_4NH(CH_2)_3NH_2 \cdot 5\text{-}TFA$ (from procedure F) were prepared via the following procedures.

| Example | m | R | Procedures |
|---------|---|------------|------------|
| 8 | 0 | ferrocene | D2, then F |
| 9 | 0 | 2-pyridine | D2, then F |
| 10 | 0 | 3-pyridine | D2, then F |
| 11 | 0 | 4-pyridine | D2, then F |
| 12 | 1 | 2-pyridine | D3, then F |

Step 9a (XIII) →

(XIV)

N-Boc nitrile XIV was prepared from nitrile XIII via amine protection using procedure A.

Step 10a

N-Boc amine 27 was prepared by hydrogenation of N-Boc nitrile XIV as N-Boc amine VIII was prepared from N-Boc nitrile VII (step 7 of this example).

EXAMPLES 6 AND 7

Starting with polyamine 20 and the appropriate R-acetic (for m=1) or carboxylic (for m=0) acid, compounds having the structure $R(CH_2)_mCO[NH(CH_2)_3]_5NH_2 \cdot 5TFA$ were prepared via procedure D1 followed by procedure F.

| Example | m | R | |
|---------|---|------------------|------------|
| 13 | 1 | 3-pyridine | D3, then F |
| 14 | 1 | 4-pyridine | D2, then F |
| 15 | 0 | 2-quinoline | D1, then F |
| 16 | 0 | 3-quinoline | D2, then F |
| 17 | 1 | 3-indole | D2, then E |
| 18 | 1 | 3-(5-hydroxyindole) | D2, then F |
| 19 | 1 | 3-(4-hydroxyindole) | D2, then E |
| 20 | 1 | 3-(5-bromoindole) | D2, then F |
| 21 | 1 | 3-(4-fluoroindole) | D2, then F |
| 22 | 0 | 2-(5-fluoroindole) | D2, then F |
| 23 | 1 | 2-(5-fluoroindole) | D2, then F |
| 24 | 1 | 3-(5-methoxyindole) | D2, then F |
| 25 | 0 | 2-quinoxaline | D2, then F |
| 26 | 0 | hydroquinone | D2, then F |
| 27 | 0 | 4-resorcinol | D2, then F |
| 28 | 1 | p-biphenyl | D2, then F |
| 29 | 1 | 2-naphthalene | D2, then F |

EXAMPLES 30 AND 31

Starting with polyamine 17 and the appropriate R-acetic or carboxylic acid, compounds having the structure $R(CH_2)_mCO[NH(CH_2)_3]_4NH_2 \cdot 4TFA$ were prepared via procedure D1 followed by procedure F.

| Example | m | R |
|---|---|---|
| 30 | 0 | ferrocene |
| 31 | 1 | 3-indole |

EXAMPLES 32 AND 33

Starting with polyamine 14 and the appropriate R-acetic or carboxylic acid, compounds having the structure $R(CH_2)_mCO[NH(CH_2)_3]_3NH_2 \cdot 3TFA$ were prepared via procedure D1 followed by procedure F.

| Example | m | R |
|---|---|---|
| 32 | 0 | ferrocene |
| 33 | 1 | 3-indole |

EXAMPLES 34 AND 35

Starting with polyamine 11 and the appropriate R-acetic or carboxylic acid, compounds having the structure $R(CH_2)_mCO[NH(CH_2)_3]_2NH_2 \cdot 2TFA$ were prepared via procedure D1 followed by procedure F.

| Example | m | R |
|---|---|---|
| 34 | 0 | ferrocene |
| 35 | 1 | 3-indole |

EXAMPLES 36 AND 37

Starting with polyamine 7 and the appropriate R-acetic or carboxylic acid, compounds having the structure $R(CH_2)_mCONH(CH_2)_3NH_2 \cdot TFA$ were prepared via procedure D1 followed by procedure F.

| Example | m | R |
|---|---|---|
| 36 | 0 | ferrocene |
| 37 | 1 | 3-indole |

EXAMPLES 38 AND 39

Starting with polyamine 23 and the appropriate R-acetic or carboxylic acid, compounds having the structure $R(CH_2)_mCO[NH(CH_2)_3]_6NH_2 \cdot 6TFA$ were prepared via procedure D1 followed by procedure F.

| Example | m | R |
|---|---|---|
| 38 | 0 | ferrocene |
| 39 | 1 | 3-indole |

EXAMPLES 40 AND 41

Starting with polyamine 26 and the appropriate R-acetic or carboxylic acid, compounds having the structure $R(CH_2)_mCO[NH(CH_2)_3]_7NH_2 \cdot 7TFA$ were prepared via procedure D1 followed by procedure F.

| Example | m | R |
|---|---|---|
| 40 | 0 | ferrocene |
| 41 | 1 | 3-indole |

PREPARATION A

Under nitrogen atmosphere, 34.5 g (157.6 mmoles) of 3-bromopropylamine.HBr in 600 ml of N,N-dimethylformamide was stirred. To that solution was added 34.4 g (157.6 mmoles) of di-tertbutyldicarbonate followed by 32.3 ml (236 mmoles) triethylamine. A precipitate formed immediately. The reaction was stirred overnight. The reaction mixture was then diluted to 1.5 liters with ethylacetate, washed once with 500 ml of 1N HCl, three times with 500 ml water, once with brine and dried over $Na_2/SO_4$. After concentration, the product was chromatographed on 800 g silica gel using 4:1 hexane/ethylacetate and the fractions were monitored by hexane/ethylacetate and the fractions were monitored by TLC ($KMNO_4/I_2$). The fractions containing the product were combined, concentrated in vacuo, chased twice with 50 ml dichloromethane and purged with high vacuum to yield 25.8 g of the product of this preparation.

We claim:

1. A compound of the formula

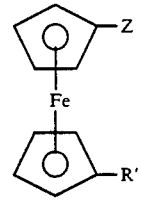

or the above substituted on the aromatic ring(s) with one or more substituents independently selected from F, Cl, Br, OH, C1 to C4 alkyl, C1 to C4 alkoxy, $CF_3$, phenyl, amino, C1 to C4 alkylamino and di(C1 to C4 alkyl)amino, or a pharmaceutically acceptable acid addition salt thereof wherein:

Z is H or R';
R' is $-(CH_2)_mCO[NH(CH_2)_n]_xNH_2$;
m is 0 or 1;
each n is independently 2 to 5; and
x is 1 to 6.

2. A pharmaceutical composition for antagonizing mammalian excitatory amino acid neurotransmitters comprising a mammalian excitatory amino acid neurotransmitter antagonizing amount of a compound according to claim 1 or a pharmaceutically acceptable acid addition salt thereof and a pharmaceutically acceptable diluent or carrier.

* * * * *